United States Patent [19]
Gouge et al.

[11] Patent Number: 5,351,831
[45] Date of Patent: * Oct. 4, 1994

[54] BAG IN A BAG FOR CONTAINERIZATION OF TOXIC OR HAZARDOUS MATERIAL

[75] Inventors: Samuel T. Gouge; James E. Shue, both of Raleigh, N.C.

[73] Assignee: Rhone-Poulenc Inc., Research Triangle Park, N.C.

[*] Notice: The portion of the term of this patent subsequent to Jun. 29, 2010 has been disclaimed.

[21] Appl. No.: 129,215

[22] Filed: Sep. 29, 1993

Related U.S. Application Data

[63] Continuation of Ser. No. 889,860, May 28, 1992, abandoned, which is a continuation-in-part of Ser. No. 803,084, Dec. 4, 1991, Pat. No. 5,222,595, which is a continuation-in-part of Ser. No. 713,684, Jun. 11, 1991, abandoned, which is a continuation-in-part of Ser. No. 680,301, Apr. 4, 1991, abandoned, which is a continuation-in-part of Ser. No. 679,290, Apr. 2, 1991, abandoned, and Ser. No. 554,615, Jul. 18, 1990, Pat. No. 5,080,226.

[51] Int. Cl.5 .................... B65D 77/04; B65D 81/32
[52] U.S. Cl. .................... 206/524.7; 206/205; 252/315.1; 424/409
[58] Field of Search .................... 206/5, 204, 205, 219, 206/524.1, 524.2, 524.6, 524.7, 525, 568, 484; 71/DIG. 1; 424/409, 412; 514/801, 812; 252/315.1

[56] References Cited

U.S. PATENT DOCUMENTS

| | | | |
|---|---|---|---|
| 3,892,905 | 7/1975 | Albert | 206/524.7 |
| 4,681,228 | 7/1987 | Kerry et al. | 206/524.7 |
| 5,080,226 | 1/1992 | Hodakowski et al. | 206/524.7 |
| 5,222,595 | 6/1993 | Gouge et al. | 206/524.7 |
| 5,253,759 | 10/1993 | Gouge et al. | 206/524.7 |

FOREIGN PATENT DOCUMENTS

| | | | |
|---|---|---|---|
| 0132726 | 2/1985 | European Pat. Off. | 206/524.7 |
| 8912587 | 12/1989 | PCT Int'l Appl. | 206/524.7 |
| 0922317 | 3/1963 | United Kingdom | 206/524.7 |

*Primary Examiner*—Jimmy G. Foster
*Attorney, Agent, or Firm*—James G. Passé

[57] ABSTRACT

The present invention relates to a containerization system comprising at least one inner water soluble (or water dispersible) bag located within an outer water soluble (or water dispersible) bag. Each water soluble bag independently contains an agrochemical that does not substantially dissolve the bag, or bags, which it contacts. Typically agrochemicals are in solid, substantially non-aqueous liquid, or organic gel form. Typical agrochemicals include plant protection compounds such as pesticides, fungicides, insecticides, acaricides, nematocides, herbicides, plant nutrients or plant growth regulators.

22 Claims, 1 Drawing Sheet

BAG IN A BAG FOR CONTAINERIZATION OF TOXIC OR HAZARDOUS MATERIAL

This is a continuation of co-pending application Ser. No. 07/889,860 filed May 28, 1992, now abandoned which application is a continuation-in-part of U.S. patent application Ser. No. 07/803,084, filed Dec. 4, 1991, now U.S. Pat. No. 5,222,595, which is a continuation-in-part of U.S. patent application Ser. No. 07/713,684, filed Jun. 11, 1991, now abandoned which is a continuation-in-part of U.S. patent application Ser. No. 07/680,301, filed Apr. 4, 1991, now abandoned which is a continuation-in-part of U.S. patent application Ser. No. 07/679,290, filed Apr. 2, 1991, now abandoned and U.S. patent application Ser. No. 07/554,615 filed Jul. 18, 1990, now U.S. Pat. No. 5,080,226, all of which are incorporated herein by reference.

BACKGROUND OF THE INVENTION

I. Field of the Invention

The invention relates to a containerization system and to containers which are particularly suitable for storing, packaging and transporting toxic or hazardous products, e.g. agricultural chemical compounds, such as pesticides and concentrates thereof.

II. Discussion of the Prior Art

At present, most hazardous and toxic liquids are stored in metal drums, or where smaller quantities are involved, in plastic containers. Hazardous compounds, especially agrochemical compounds, are formulated in various compositions.

The expression toxic or hazardous compounds as used herein means an industrial chemical or agrochemical compound which, if released in the quantity or concentration normally in storage and shipping containers, may cause damage to the environment or be injurious to a person contacted by it.

With respect to agricultural chemicals, liquid compositions, particularly in the form of concentrates, are most convenient for farmers because of the relative ease with which they can be handled. There are, nevertheless, difficulties in handling such liquid compositions. There is a danger of spillage or leakage if holes develop in containers that are accidentally dropped and thereby crack or fail. Containers have been developed which possess great resistance to impact and shock. While such containers are secure under normal storage and handling conditions, in the event of an accident, for example during transporting, there remains an appreciable risk of spillage or leakage with rapid loss of liquid. Leakage of toxic and hazardous chemicals can create damage to the environment.

The chemical and packaging industries have long sought a secure container which provides sufficient safeguard for those handling it, such as farmers and transporters, as well as adequate protection of the environment. It is known, for example, to package agrochemicals in soluble bags or sachets made from water soluble films. However, there are some cases whereby the use of water soluble (or water dispersible, as always contemplated herein) bags is either impossible or of highly limited interest. This is or can be the situation when two or more agrochemicals are used together to treat a crop or any kind of plant(s) and when only one of them is used in the form of a water soluble bag. It is also or can be also the situation when two or more agrochemicals are used together to treat a crop or any kind of plant(s) and when the normal use of these agrochemicals is at a very different use rate. Indeed it is known that the use rate of some pesticides may vary on the order of 10 or even 100 times from one pesticide to another.

Another situation where the use of a water soluble bag for a pesticide has been considered up to now of no interest is the situation whereby incompatible agrochemicals are used. Incompatible agrochemicals are agrochemicals which, when added together in a concentrated form or in a tank for mixing, at least partially, agglomerate together and/or produce sediment at the bottom of the tank without being dispersed or emulsified in the tank when stirred. Other kinds of incompatible agrochemicals are agrochemicals which are chemically unstable when mixed together over time.

In the art of detergency or laundry, it is known to used systems with one inner bag, or sachet, in an outer pouch (e.g., U.S. Pat. No. 4,846,992 or European patent application 132726), however these known systems comprise an outer water-permeable pouch or bag. Such water permeable pouches are in fact water-insoluble, and thus they are not appropriate for uses wherein the whole containerization system has to disappear when put in water. This is especially the situation of farmers who disperse agrochemicals in water tanks in order to obtain a spraying mixture.

Unfortunately the use of more than one agrochemical by farmers to treat their crop is more and more common, and the farmers like very much the so-called ready-mix which are mixtures that the farmers may use directly for dilution in their tank. Thus, the ready mix practice does not yet fit to the water soluble bag technology.

SUMMARY OF THE INVENTION

The present invention relates to a containerization system comprising at least one inner water soluble bag located within an outer water soluble bag. Each water soluble bag independently contains an agrochemical that does not dissolve the bag, or bags, which it contacts. Typical agrochemicals are in solid, liquid (preferred when substantially non-aqueous), or organic gel form. Typical agrochemicals include plant protection agents or compounds such as pesticides (for example, insecticides, fungicides, herbicides, acaricides, nematocides), plant nutrients or plant growth regulators.

An object of the instant invention is to provide a new containerization system to contain agrochemicals which is safe for everybody.

Another object of the instant invention is to provide a new containerization system to contain agrochemicals which is easy for the farmer to manipulate.

Another object of the instant invention is to provide a new containerization system to contain agrochemicals which is readily, rapidly and easily soluble and/or dispersible in water.

Another object of the instant invention is to provide a new containerization system to contain agrochemicals which is as much condensed as possible, using the least amount of space.

Another object of the instant invention is to provide a new containerization system and/or a new method to contain more than one hazardous compound, e.g. agrochemicals, which diminishes the risks of pollution.

Another object of the instant invention is to provide a new containerization system to contain two or three hazardous compounds, e.g., agrochemicals.

Another object of the instant invention is to provide a new containerization system to contain two or three hazardous compounds, e.g., agrochemicals, which are normally used at different use rates.

Another object of the instant invention is to provide a new system to contain two or three hazardous compounds, e.g., agrochemicals, which are normally incompatible.

Another object of the instant invention is to provide a new system for containing chemicals such as agrochemicals which enables such chemicals to be easily and homogeneously dispersed in water even though they may be incompatible.

Another object of the present invention is to provide a new system for containing chemicals such as agrochemicals which enables such chemicals to be easily and homogenously dispersed in water even though they may be present in a different or very different amount.

A further object of the present invention is to provide a containerization system wherein less solvent is needed in the formulation of an agrochemical, which is a cost saving both in shipping and manufacturing.

A further object of the present invention is to provide a new containerization system for agrochemicals which eliminates, or at least reduces, the disagreeable odors or odor problems of odoriferous chemicals.

A further object of the present invention is to provide a new containerization system for agrochemicals which eliminates, or at least reduces, the waste disposal of contaminated containers and overpacks.

A further object of the present invention is to provide a new containerization system for agrochemicals which quickly dissolves when put into water.

The invention further seeks to provide a new containerization system for agrochemicals which reduces the risks of clogging the spray nozzles or the filters of spray tanks.

Other objects of the invention will better appear from the following description.

The objects of the invention can be achieved in full or in part by means of the invention.

BRIEF DESCRIPTION OF THE DRAWINGS

FIG. 1 and 2 illustrate, but are not intended to limit, the present invention.

DETAILED DESCRIPTION OF THE INVENTION

Figure 1:
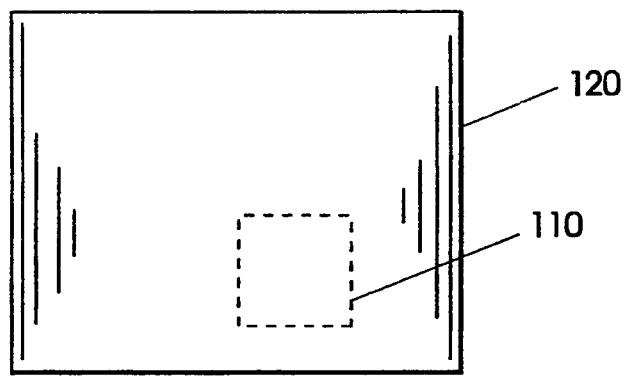
FIG. 1 is a front view which schematically shows an embodiment of the present invention having an inner bag 110 located within an outer bag 120.
Figure 2:
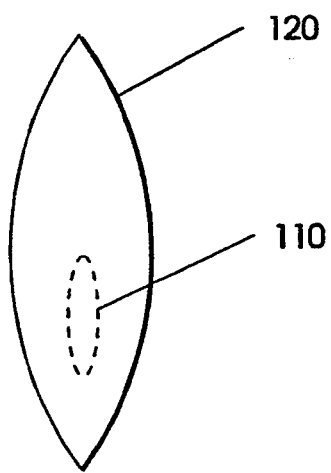
FIG. 2 is a side view of the embodiment of FIG. 1.

The containerization system of the present invention comprises at least one (preferably one or two) inner water soluble or water dispersible bags containing a hazardous compound or product, preferably an agrochemical, more preferably a non-aqueous agrochemical.

The containerization system further comprises an outer water soluble or water dispersible bag containing another hazardous compound or product (different from the first hazardous compound), preferably an agrochemical, more preferably a non-aqueous agrochemical. The outer bag also contains the inner bag with its content. Optionally, this so-called "poly-bag system" is itself contained in an external water insoluble container, such as a rigid or semi-rigid box.

The hazardous compounds or products of the invention and the wall of the bags they contact are chose so that the hazardous compounds or products do not substantially dissolve the wall of the bag they contact and do not substantially permeate through it. By this it is meant that the dissolution and permeation are each independently less than 5%, more preferably less than 1% and most preferably less than 0.5% of the total weight of the bag.

The hazardous compounds of this invention, especially the agrochemical compositions, which are contained in the bags according to the invention are essentially materials containing 0.5 to 80% (w/w) of active ingredient (such as plant protection agents or pesticides or plant growth regulators or plant nutrients, as hereafter defined) and these agrochemical compositions are concentrated compositions which are supposed to be diluted in water before spraying.

The agrochemical compositions which may be used in the invention and which may be contained in the outer or the inner container may be in different physical forms. They may be in the form of a solid such as powders, preferably water wettable powders, or granules, preferably water dispersible granules; or they may be in the form of a non-aqueous liquid, such as a solution or a dispersion or an emulsion in an organic solvent. This liquid may be more or less viscous; it may be a very fluid liquid such as a liquid having a Brookfield viscosity between 100 and 1,000 centipoise, or it may be a viscous liquid, such as a liquid having a Brookfield viscosity from 1,000 up to 30,000 centipoise (Measurement of viscosities in this specification are made with a Brookfield viscosimeter at 23° C. with a flat plate rotating at 20 revolutions per minute). A further advantageous physical form of the agrochemical composition is the form of an organic gel.

Gels which are of particular interest in the invention are organic gels which have viscosities of 600 to 30,000 centipoise, preferably 1,000 to 12,000 centipoise, and still more preferably 1,000 to 5,000 centipoise.

According to another aspect of the invention, the material or gel which is used in the invention is essentially a material which has a phase difference phi between the controlled shear stress and the resulting shear strain such that tg(phi) is less than or equal to 1.5, preferably less than or equal to 1.2. Tg(phi) is the tangent of the phi angle (or phase difference). The measurement of phi is made by means of a rheometer having a flat fixed plate and a rotating cone above this plate such that the angle between them is less than 10°, preferably less than 4. The cone is caused to rotate by means of a controlled speed motor; the rotation is a sinusoidal one, i.e., the torque and the angular displacement change as a sine function with time. This angular displacement corresponds to the hereabove mentioned shear strain; the torque of the controlled speed motor (which causes the angular displacement) corresponds to the hereabove mentioned controlled shear stress.

It is known that a gel is generally a colloid in which the dispersed phase has combined with the continuous phase to produce a viscous, jelly-like product; it is also a dispersed system consisting typically of a high molecular weight compound or aggregate of small particles in very close associate with a liquid. The gels used in the invention have basically an organic continuous phase. In contrast, most of the existing materials/gels are water-based and have an aqueous continuous phase. Furthermore, the gels used in the invention have essentially one physical phase, at least as can be seen when visually observed. Preferred gels in the invention are also gels which can be divided by cutting and whose cut parts are able to merge together by simple juxtaposition.

The non-aqueous agrochemical compositions which are used in the invention are essentially materials having a low water content, generally less than 5% (by weight), preferably less than 3%, more preferably less than 1%.

The choice of the particular physical form of the agrochemicals used in the invention depends of the particular agrochemicals which are involved.

The following features, alone or in combination, constitute preferred features of the invention:

According to one feature, the hazardous product is preferably an agrochemical, or more precisely a plant protection agent (including pesticides, such as insecticides, fungicides, herbicides, acaricides or nematocides; or plant growth regulators or plant nutrients).

The invention is not limited to some specific agrochemicals; a list of many agrochemicals which can be used in the poly-bag system of the invention includes:

fungicides such as triadimefon, tebuconazole, prochloraz, triforine, tridemorph, propiconazole, pirimicarb, iprodione, metalaxyl, bitertanol, iprobenfos, flusilazol, fosetyl, propyzamide, chlorothalonil, dichlone, mancozeb, anthraquinone, maneb, vinclozolin, fenarimol, bendiocarb, captafol, benalaxyl, thiram;

herbicides (or defoliants) such as quizalofop and its derivatives, acetochlor, metolachlor, imazapur and imazapyr, glyphosate and gluphosinate, butachlor, acifluorfen, oxyfluorfen, butralin, fluazifop-butyl, bifenox, bromoxynil, ioxynil, diflufenica, phenmedipham, desmedipham, oxadiazon, mecoprop, MCPA, MCPB, linuron, isoproturon, flamprop and its derivatives, ethofumesate, diallate, crabetimide, alachlor, metsulfuron, chlorsulfuron, chlorpyralid, 2,4-D, tribufos, triclopyr, diclofop-methyl, sethoxydim, pendimethanlin, trifluralin, ametryn chloramben, amitrole, asulam, dicamba, entazone, atrazine, cyanizine, thiobencarb, prometryn, 2-(2-chlorobenzyl)-4,4-dimethyl-1,2-oxazolidin-3-one, fluometuron, napropamide, paraquat, bentazole, molinate, propachlor, imazaquin, metribuzin, tebuthiuron, oryzalin; insecticides or nematicides such as ebufos, carbosulfan, amitraz, vamidothion, ethion, triazophos, propoxur, phosalone, permethrin, cypermethrin, parathion, methylparathion, diazinon, methomyl, malathion, lindane, fenvalerate, ethosprophos, endrin, endosulfan, dimethoate, dieldrin, dicrotophos, dichlorprop, dichlorvos, azinphos and its derivatives, aldrin, cyfluthrin, deltamethrin, disulfoton, chlordimeform, chlorpyrifos, carbaryl, dicofol, thiodicarb, propargite, demeton, phosalone; and plant growth regulators such as gibbeleric acid, ethrel or ethephon, cycocel, chlromequat, ethephon, mepiquat.

According to another feature, the ratio of volume between the outer bag and the inner bag is more than 1.5:1, preferably more than 2:1.

According to another feature, the ratio of weight of agrochemicals contained respectively in the outer bag and in the inner bag(s) is approximately equal to the ratio of the use rates of (or recommended for) the active ingredients contained respectively in the outer bag and the inner bag(s). Approximately equal means equal to the said ratio of the use rates or to a value which is in the range of plus or minus 10% of the said ratio of the use rates.

According to another feature of the invention the inner bag(s) and the outer bag contain respectively incompatible hazardous products, especially incompatible agrochemicals.

According to another feature of the invention both outer and inner bags can float or sink when put into water, such as the tank of water that a farmer uses for mixing and spraying.

According to still another feature of the invention which is particularly appropriate for incompatible or very incompatible agrochemicals, one of the bags (either an inner bag or the outer bag) floats and the other (or its content; preferably the outer bag) sinks when put into water. These specific bags are particularly suitable for very incompatible agrochemicals, whereby these incompatible agrochemicals, due to the fact that one bag floats and the other sinks, are separately diluted and mixed with water before being intermixed with each other.

When it is said that the inner bag floats and the outer bag sinks when put into water, this means that, when put into water, the inner bag(s) filled with its content, or its content alone (when the said inner bag has dissolved), float(s) when the outer bag is open (that is to say when the enveloping film of the outer bag has dissolved enough to let its content move) and when, at the same time, this partially opened outer bag (before it has completely dissolved) and its content (before or after this outer bag has completely dissolved) sink.

When it is said that the outer bag floats and the inner bag(s) sinks when put into water, this means that, when put into water, the inner bag(s) filled with its content, or its content alone (when the said inner bag has dissolved), sink(s) when the outer bag is open (that is to say when the enveloping film of the outer bag has dissolved enough to let its content move) and when, at the same time, this partially opened outer bag (before it has completely dissolved) and its content (before or after this inner bag has completely dissolved) float.

According to a particular feature of the invention, wherein one bag is floating and the other is sinking, the floating bag contains a liquid or a gel or, according to an advantageous feature, it contains a wettable powder or water dispersible granules.

According to a particular feature of the invention which is of particular interest, the bags of the invention are made in such a way that the outer bag, either with its full content or with only the agrochemical composition which is outside the inner bag, may have a specific gravity greater than 1 and the inner bag, with its content, may have a specific gravity less than 1.

According to a particular feature of the invention which is of particular interest, the bags of the invention are made in such a way that the outer bag, either with its full content or with only the agrochemical composition which is outside the inner bag, with its content, may have a specific gravity greater than 1.

According to another feature, the bags of the invention, especially the outer bag, are filled to at least 60% of capacity with the agrochemical composition, more preferably to at least 70% of capacity, still more preferably 80 to 99% of capacity and most preferably 85 to 95% of capacity. The outer bag is preferably not filled to complete capacity because the unused capacity gives the shock resistance, i.e., resistance to breakage when dropped, transported or stored. This unused capacity may or may not contain air or inert gas. An absence of air or inert gas in the unused capacity further improves shock resistance. However, in deciding how much unused capacity, or absence of air or inert gas, to provide, the advantages of shock resistance must be balanced against the need, if any for shock resistance and the cost of providing shock resistance. For example, if the outer bag is stored and/or transported in a shock absorbing container, then it may not be as helpful to provide this unused capacity.

Also, the capacity to which the outer bag is filled, and whether the unused capacity does or does not contain air is affected by whether it is desired to have the bag sink or float.

Whether the bag sinks or floats will depend not only on the unused capacity, but also the specific gravity of the bag contents.

The percentage of capacity to which the inner bag is filled is more dictated, than is the capacity of the outer bag, by whether it is desired that the inner bag would sink or float. For example, compatibility of the bag contents and dispersibility of the bag contents in water affects whether it is desired to have the inner bag and the outer bag float, or both sink, or have one bag sink and the other bag float. For example, if the active ingredients, or their formulations, contained by the inner or outer bags are compatible and dispersible even if both bags break open in the same part of the mixing bath, then it may be desirable to have both bags float or both bags sink.

When the bag is filled with solids, the capacity is relative to bulk volume of the solids, not the actual particle volume of the solids.

According to another feature of the invention, the inner bag may contain a marker, e.g., a dye. This marker is released to show if the inner bag has failed for any reason so that the package should not be used.

In practice, the agrochemical compositions used in the instant invention generally comprises the active ingredient(s) in association with other ingredients, for example, surfactants, dispersants, thickeners, antifoaming, antifreezing, gelled agents or gelling agents and plasticizers of the polymeric material constituting the enveloping film of the bags.

According to another feature the bags used in the invention are preferably made of a polymeric water soluble film. The thickness of this film is generally between 10 and 500 microns, preferably between 20 and 100 microns.

The polymeric material constituting the wall of the bags may be the same or may be different for the two bags. even though these two bags may be different, they are preferably cold water soluble. Cold water soluble means completely soluble in water at a temperature lower than 35° C., for example comprised between 5° C. and 35° C. Both inner and outer bags may dissolve in water under similar conditions, that is to say in the same range of temperature as hereinbefore defined.

The chemical nature of the enveloping film constituting the bags can vary quite widely. Suitable materials are water soluble (or possibly water dispersible) materials which are insoluble in the organic solvents used to dissolve or disperse the agrochemical active ingredient. Specific suitable materials include polyethylene oxide, such as polyethylene glycol; starch and modified starch; alkyl and hydroxyalkylcellulose, such as hydroxymethylcellulose, hydroxyethylcellulose, hydroxypropyl cellulose; carboxymethylcellulose; polyvinylethers such as poly methyl vinylether or poly(2-methoxyethoxyethylene); poly(2,4-dimethyl-6-triazinylethylene; poly(3-morpholinyl ethylene); poly(N-1,2,4-triazolyethylene); poly(vinylsulfonic acid); polyanhydrides; low molecular weight melamine-formaldehyde resins; low molecular weight urea-formaldehyde resins; poly(2-hydroxyethyl methacrylate); polyacrylic acid and its homologs. Preferably the enveloping film comprises or is made from polyvinylalcohol (PVA). PVA is generally partially or fully alcoholysed or hydrolysed, e.g., 40–100%, preferably 80–99% alcoholysed or hydrolysed, polyvinyl acetate (or other ester) film; copolymers or other derivatives of such polymers can also be used.

Preferred materials for constituting the bags in the invention are polyethylene oxide or methylcellulose, or polyvinylalcohol. When polyvinylalcohol is used, it is advantageously a 40–100% alcoholysed or hydrolysed, preferably 80–99% alcoholysed or hydrolysed, polyvinyl acetate film.

The poly-bag system of the instant invention may be used by the farmer by simply putting the system into a tank of water and mixing or recirculating to get the ingredients homogeneously dispersed.

Accordingly, by another feature of the present invention, the poly-bag system is put into a tank of water. Then the farmer waits until the inner bag disassociates from the outer bag and its contents start to leak out. Then the mixing or recirculating starts only after that time. As already said, the bags may float or sink.

An advantage of the instant invention is that it prevent users from opening one package and trying to use only a part of one or the other package. Thus the invention provides a far safer system to apply two compounds to crops. It is safer both for the user and for the crop or plant.

The preparation or manufacturing of the containerization system of the invention can be done according the known process of preparation or manufacturing of water soluble bags. As a practical manner, the first bag (that is to say the inner bag, or inner bags if more than one) is prepared from a water soluble film, optionally by partial heat sealing. Then it is filled with an agrochemical composition and the bag(s) is finally closed. Then the second bag (that is to say the outer bag) is prepared in the same way. However it is filled not only by an agrochemical composition, but also with the first bag(s) previously prepared. This later outer bag is also closed, preferably by heat sealing.

An advantage of the present invention is that it provides an easy way to obtain a two-components active unit. Its manufacturing is rather easy and does not need a real mixing system.

The following examples are given for illustrative purposes and should not be understood as restricting the invention.

In these examples, the Brookfield viscosity was measured, as previously indicated, with a Brookfield viscosimeter which had a flat plate rotating at 20 revolutions per minute.

In all the following examples, the prepared gels had a tg(phi) of between 0.1 and 1.5.

Further information may be found in the following applications, the disclosures of which are incorporated herein by reference: U.S. Ser. No. 07/713,681 (pending), application of David B. Edwards, William J. McCarthy, Leonard E. Hodakowski, Chi-Yu R. Chen, Samuel T. Gouge and Paul J. Weber for "Laminated Bags for Containerization of Toxic or Hazardous Materials" filed Jun. 11, 1991; U.S. Ser. No. 07/713,682

(pending), application of Samuel T. Gouge, Leonard E. Hodakowski, Paul J. Weber and Chi-Yu R. Chen for "Gel Formulations for Hazardous Products" filed Jun. 11, 1991; U.S. Ser. No. 07/713,701 (allowed), application of Leonard E. Hodakowski, Chi-Yu R. Chen, Samuel T. Gouge and Paul J. Weber for "Water Dispersible Gel Formulations" filed Jun. 11, 1991; U.S. Ser. No. 07/713,685 (pending), application of Leonard E. Hodakowski, Ricky W. Couch, Samuel T. Gouge and Robert C. Ligon for "Gel Formulations" filed Jun. 11, 1991; and U.S. Ser. No. 07/713,683 (pending), application of Leonard E. Hodakowski, Chi-Yu R. Chen, Samuel T. Gouge and Paul J. Weber for "Gel Formulations for Use in Toxic or Hazardous Product Containerization Systems" filed Jun. 11, 1991.

EXAMPLE 1

A package was made by placing a water soluble bag filled with a solid material into a large water soluble bag filled with a gel.

A herbicidal wettable powder containing the herbicide known as atrazine was placed in a so-called inner bag (10 g of a wettable powder whose particles have a size less than 5 microns).

This wettable powder was poured into a small polyvinyl alcohol water soluble bag. This material was sealed with a small pocket of air to ensure the bag would float.

The second herbicide was 1 liter of a gel containing 460 g bromoxynil (in the form of octanoate ester). It was poured into a polyvinyl alcohol water soluble bag. The previous bag with atrazine was also added into this bag (hereafter the smaller bag is going to float on the gel surface). This larger bag was then sealed.

The film used in this experiment was a laminated film of polyvinyl alcohol with a thickness of 75 microns. Both the small and large bags were made with this film by heat sealing.

The two sealed bags were placed into a tank filled with 20 gallons of 342 ppm (calcium and magnesium chloride content) hard water. The contents immediately sank to the bottom of the tank and began to dissolve. After approximately 1 minute and 28 seconds, the outer bag released a small pocket of air. After another 15 seconds the atrazine spilled from the dissolving water soluble bag and dispersed in a cloud into the clear water. Immediately after the release of the atrazine wettable powder, the recirculation pump was started that dispersed the gel laying on the tank bottom with the diluted atrazine. This recirculation was continued for 4 minutes. Then all contents of the tank was sprayed through the spray nozzles. There was no bag film nor products left in filters or on the tank bottom.

EXAMPLE 2

A package was made by placing a water soluble bag filled with a gel insecticide into a large water soluble bag filled with a solid water dispersible granule insecticide.

The film used in this experiment was a laminated film of polyvinyl alcohol with a total thickness of 75 microns.

15 g of a cypermethrin gel was poured into a small water soluble bag made of polyvinyl alcohol. This gel contained surfactants in a sufficient amount so as to promote dispersion and emulsion of the gel when diluted into water.

1000 g of thiodicarb water dispersible granule was poured into a large water soluble polyvinyl alcohol bag. The smaller bag filled with the cypermethrin was also added to this large bag filled with thiodicarb water dispersible granule. This large bag was then sealed by heat sealing.

This large bag with its content was dropped into a tank filled to 18 gallons of water with 342 ppm hardness. This large bag floated on the water surface. This bag began to dissolve and after approximately 1.25 minutes, small amounts of the water dispersible granules began to drop from the large bag. After an additional 15 seconds, the small bag (filled with pyrethroid) was also released from the dissolving bag. This small bag dissolved allowing the gel to flow from it onto the water surface. This gel quickly mixed with the water as soon as the recirculation pump was turned on. After approximately 2 additional minutes of recirculation, the floating water dispersible granules dispersed completely into the water mix. There were no problems observed by nozzle pluggage or by screen blockage or by sediment left on the tank bottom.

In this example, the water dispersible granule, as well as the wettable powder of the Example 1, are floating because of their air content.

EXAMPLE 3

A package was made by placing a water soluble bag filled with a water-dispersible herbicide (sulfonylurea) into a larger water soluble bag filled with a gel of bromoxynil similar to that of Example 1.

The film used in this experiment was a laminated film of polyvinyl alcohol with a total thickness of 75 microns. 8 g of a sulfonylurea water dispersible granule herbicide was used to fill a small water soluble polyvinylalcohol bag. The bag was then heat sealed.

950 ml of a bromoxynil gelled herbicide was poured into a larger water soluble bag made of polyvinyl alcohol. The smaller bag filled with the sulfonylurea was also placed inside this larger bag filled with the bromoxynil gel. This large bag with its content was then heat sealed.

This large bag with its content was dropped into a tank of water (18 gallons). This large bag sank to the tank bottom and began to dissolve. After approximately 1.5 minutes, it released a small pocket of air. Twelve (12) seconds later, the small bag full of sulfonylurea water dispersible granules floated to the top of the water surface. Approximately 1 minute and 2 seconds later, the sulfonylurea water dispersible granules began to spill out of the dissolving polyvinylalcohol bag and disperse into water. After an additional 17 seconds, the water dispersible granules had wetted in water and dispersed into water. The pump recirculation system was started. This immediately mixed the gel into the tank of water with the sulfonyl urea. The mixture was sprayed through the nozzles and final examination showed no sedimentation or pluggage in the nozzles, filters or on the tank bottom.

EXAMPLE 4

A package was made by placing a water soluble bag filled with a liquid insecticide into a larger water soluble bag filled with a solid water dispersible granule insecticide.

The film used in this experiment was a laminated film of polyvinyl alcohol with a total thickness of 75 microns.

12 g of a cypermethrin emulsifiable concentrate (460 g of pyrethroid per liter) was poured into a small water soluble bag made of polyvinyl alcohol. This material was sealed close to the liquid level to remove as much trapped air as possible.

1200 g of carbaryl wettable powder (80% of carbaryl in the powder) was poured into a large water soluble polyvinyl alcohol bag. The smaller bag filled with the cypermethrin was also added to this large bag filled with carbaryl water dispersible granule. This large bag was then sealed by heat sealing.

This large bag with its content was dropped into a tank filled to 18 gallons with water (hardness: 342 ppm). This large bag floated on the water surface. This bag began to dissolve and, after approximately 1 minute 24 seconds, released its contents including the small bag (filled with pyrethroid). This small bag began to dissolve into the cloudy water mixture. After 1 minute 10 seconds the liquid broke and diluted itself into the water. The pump recirculation was started and the materials readily mixed inside the tank.

The contents was sprayed through the nozzles and final examination showed no sedimentation or pluggage or residue in the nozzles, filters, or in the tank bottom.

What is claimed is:

1. A containerization system which comprises at least one inner water soluble or water dispersible bag containing a hazardous compound, the containerization system further comprising an outer water soluble or water dispersible bag containing another hazardous compound different from the first and incompatible with it, the outer bag also containing the inner bag with its content.

2. A containerization system which comprises at least one inner water soluble or water dispersible bag containing a hazardous compound, the containerization system further comprising an outer water soluble or water dispersible bag containing another hazardous compound different from the first and incompatible with it, the outer bag also containing the inner bag with its content, and wherein the hazardous compounds and the wall of the bags they contact are chosen so that the hazardous compounds do not substantially dissolve the wall of the bag they contact and do not substantially permeate through it.

3. A containerization system according to claim 1 wherein the hazardous compounds are agrochemical compounds and wherein has the agrochemical compounds and the wall of the bags they contact are chosen so that the agrochemical compounds do not substantially dissolve the wall of the bag they contact and do not substantially permeate through it.

4. A containerization system according to claim 1 wherein the hazardous compounds comprise agrochemicals and wherein has the agrochemicals are chosen from the group comprising plant protection agents, pesticides, insecticides, fungicides, herbicides, acaricides, nematocides, plant growth regulators and plant nutrients.

5. A containerization system according to claim 1 in which said at least one inner water soluble or water dispersible bag comprises one or two inner cold water soluble or cold water dispersible bags containing said hazardous compound, and in which said outer water soluble or water dispersible bag comprises one outer cold water soluble or cold water dispersible bag containing said another hazardous compound different from the one or two inner bags.

6. A containerization system according to any one of claims 1 to 5, which comprises a further water insoluble external container.

7. A containerization system according to any one of claims 1 to 5, wherein the hazardous compounds or agrochemicals in the bags are in solid and/or liquid and/or gel form.

8. A containerization system according to any one of claims 1 to 5, wherein the hazardous compounds or agrochemicals are in a concentrated form.

9. A containerization system according to any one of claims 1 to 5, wherein at least one bag contains an agrochemical composition in the form of water wettable powder or water dispersible granule.

10. A containerization system according to any one of claims 1 to 5, wherein one bag contains a non-aqueous liquid in the form of a solution or a dispersion or an emulsion.

11. A containerization system according to any one of claims 1 to 5, wherein the ratio of weight of the hazardous compounds or agrochemicals contained respectively in the outer bag and in the inner bag is equal to a value which is in the range of plus or minus 10% of the ratio of the use rates of the active ingredients contained respectively in the outer bag and the inner bag.

12. A containerization system according to any one of claims 1 to 5, wherein the ratio of volume between the outer bag and the inner bag is more than 1.5:1.

13. A containerization system according to any one of claims 1 to 5, wherein the ratio of volume between the outer bag and the inner bag is more than 2:1.

14. A containerization system according to any one of claims 1 to 5, wherein at least one bag contains an agrochemical composition in the form of a non-aqueous liquid or in the form of an organic gel.

15. A containerization system according to any one of claims 1 to 5, wherein at least one bag contains an agrochemical composition in the form of an organic gel, and the organic gel has a viscosity of 600 to 30,000 centipoise.

16. A containerization system according to any one of claims 1 to 5, wherein at least one bag contains an agrochemical composition in the form of an organic gel, and the organic gel has a viscosity of 1,000 to 12,000 centipoise.

17. A containerization system according to any one of claims 1 to 5, wherein at least one of the compositions is an organic gel, and the organic gel has a phase difference phi between the controlled shear stress and the resulting shear strain such that tg(phi) is less than or equal to 1.5.

18. A containerization system according to any one of claims 1 to 5, wherein at least one of the compositions is an organic gel, and the organic gel has a phase difference phi between the controlled shear stress and the resulting shear strain such that tg(phi) is less than or equal to 1.2.

19. A containerization system according to any one of claims 1 to 5, wherein the inner bag contains a marker.

20. A containerization system according to any one of claims 1 to 5, wherein the outer bag is filled with an agrochemical and said inner bag to at least 60% of capacity.

21. A containerization system according to any one of claims 1 to 5, wherein at least one of the agrochemical compositions is a liquid which has a Brookfield viscosity between 100 and 30,000 centipoise.

22. A containerization system according to any one of claims 1 to 5, wherein at least one of the compositions is a liquid which has a Brookfield viscosity between 1,000 and 30,000 centipoise.

* * * * *